(12) United States Patent
Huff et al.

(10) Patent No.: US 7,130,699 B2
(45) Date of Patent: Oct. 31, 2006

(54) MEDICAL LEAD ADAPTOR ASSEMBLY

(75) Inventors: Eric W. Huff, St. Paul, MN (US);
Andrew J. Ries, Lino Lakes, MN (US);
Frank L. Skubitz, Andover, MN (US);
Timothy W. Holleman, Ham Lake,
MN (US); Timothy C. Aarons, Maple
Grove, MN (US); **Bruce R.
Mehdizadeh**, Savage, MN (US)

(73) Assignee: Medtronic, Inc., Minneapolis, MN (US)

( * ) Notice: Subject to any disclaimer, the term of this patent is extended or adjusted under 35 U.S.C. 154(b) by 491 days.

(21) Appl. No.: 10/436,776

(22) Filed: May 13, 2003

(65) Prior Publication Data

US 2004/0230268 A1 Nov. 18, 2004

(51) Int. Cl.
*A61N 1/00* (2006.01)

(52) U.S. Cl. .......................... 607/116; 607/10; 607/115; 607/119; 607/122

(58) Field of Classification Search .............. 607/116, 607/115, 122, 909, 119, 123, 10
See application file for complete search history.

(56) References Cited

U.S. PATENT DOCUMENTS

| | | | | |
|---|---|---|---|---|
| 4,744,370 A * | 5/1988 | Harris | ........................ | 607/122 |
| 4,744,371 A * | 5/1988 | Harris | ........................ | 607/117 |
| 4,944,088 A | 7/1990 | Doan et al. | .................... | 29/858 |
| 4,951,687 A | 8/1990 | Ufford et al. | ............... | 128/786 |
| 5,007,435 A | 4/1991 | Doan et al. | .................. | 128/784 |
| 5,211,637 A * | 5/1993 | Goto et al. | .................. | 604/533 |
| 5,234,359 A | 8/1993 | Takahashi et al. | .......... | 439/481 |
| 5,241,957 A | 9/1993 | Camps et al. | ................ | 607/119 |
| 5,348,481 A | 9/1994 | Ortiz | ........................... | 439/25 |
| 5,354,326 A | 10/1994 | Comben et al. | ............ | 607/115 |
| 5,560,358 A | 10/1996 | Arnold et al. | ............... | 128/642 |
| 5,782,892 A | 7/1998 | Castle et al. | ................... | 607/37 |
| 5,843,141 A | 12/1998 | Bischoff et al. | .............. | 607/37 |
| 5,931,861 A | 8/1999 | Werner et al. | .............. | 607/115 |
| 6,038,479 A | 3/2000 | Werner et al. | .............. | 607/115 |
| 6,038,481 A | 3/2000 | Werner et al. | .............. | 607/119 |
| 6,192,278 B1 | 2/2001 | Werner et al. | .............. | 607/115 |
| 6,343,233 B1 | 1/2002 | Werner et al. | .............. | 607/119 |
| 6,397,108 B1 | 5/2002 | Camps et al. | ............... | 607/115 |
| 6,466,824 B1 | 10/2002 | Struble | ....................... | 607/115 |
| 6,708,067 B1 * | 3/2004 | Bisping | ...................... | 607/119 |
| 6,921,295 B1 * | 7/2005 | Sommer et al. | ............ | 439/668 |
| 2003/0120327 A1 | 6/2003 | Tobritzhofer et al. | ....... | 607/116 |
| 2003/0199948 A1 * | 10/2003 | Kokones et al. | ............ | 607/117 |

* cited by examiner

*Primary Examiner*—Robert Pezzuto
*Assistant Examiner*—Shevon Johnson
(74) *Attorney, Agent, or Firm*—Carol F. Barry; Girma Wolde-Michael

(57) ABSTRACT

A medical lead adapter assembly is provided for facilitating an electrical connection between an implantable medical lead connector and an external medical device. The adapter includes a housing, having a sidewall and a longitudinally extending connector receptacle, and at least one contact opening passing through the sidewall to the receptacle. The contact opening is positioned in a location corresponding with at least one ring contact of the lead connector, when the lead connector is engaged within the receptacle, and allows electrical connection between at least one contact element of the external medical device and the at least one ring contact of the lead connector.

23 Claims, 19 Drawing Sheets

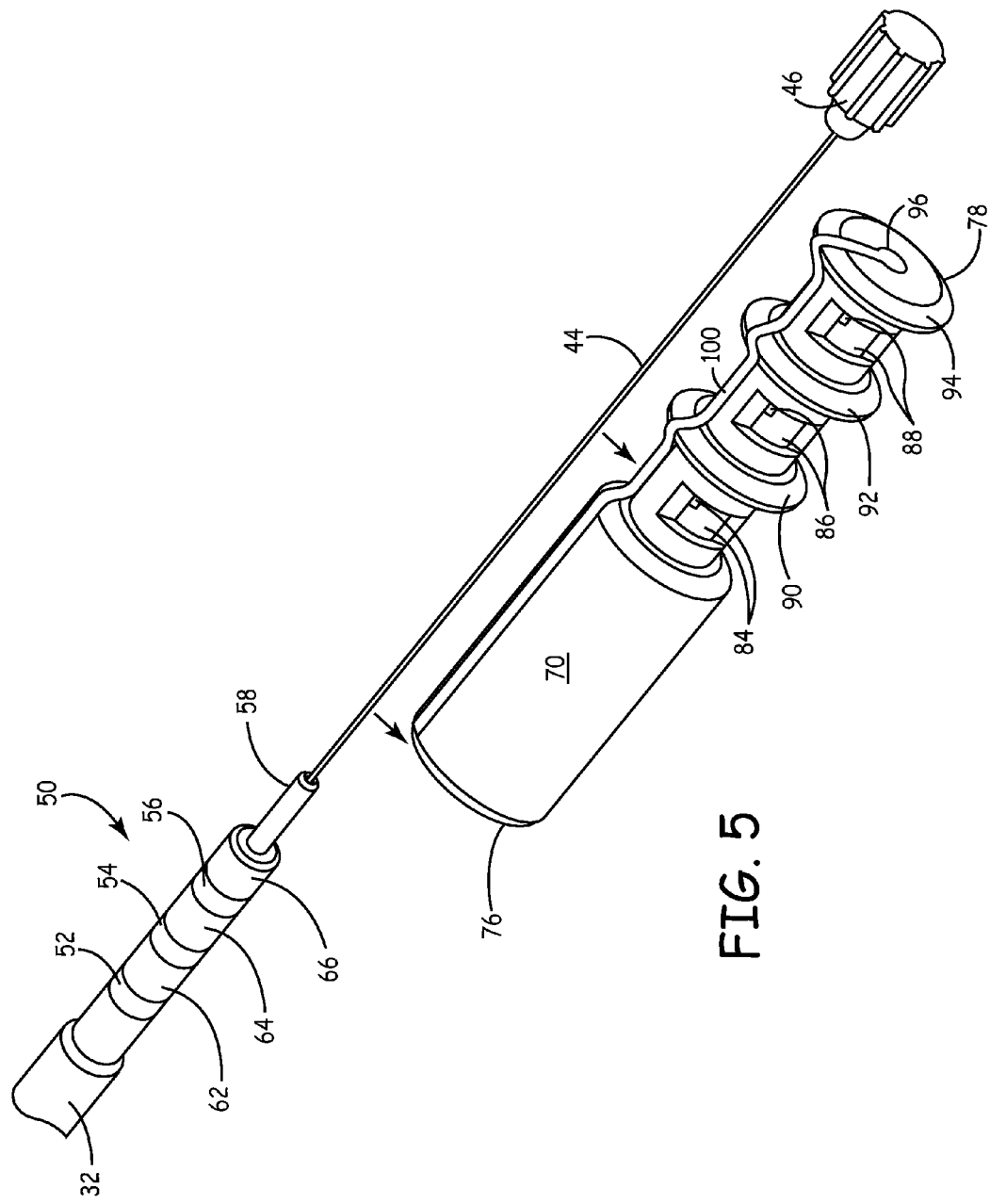

MEDICAL LEAD ADAPTOR ASSEMBLY

CROSS REFERENCE TO RELATED APPLICATION

Cross-reference is hereby made to commonly assigned related U.S. applications filed concurrently herewith: Ser. No. 10/436,770 to William Wenger, entitled "Medical Lead Adaptor Assembly" and Ser. No. 10,436,960 to Frank Skubitz et al., entitled "Medical Lead Adaptor Assembly".

FIELD OF THE INVENTION

The present invention generally relates to a medical lead adaptor assembly, and in particular, the present invention relates to a medical lead adaptor assembly for making a temporary connection between a medical lead of an implantable medical device and an external medical device.

BACKGROUND OF THE INVENTION

The earliest instances of relatively prolonged cardiac stimulation, namely cardiac pacing, of a patient's heart was effected through implanted cardiac leads attached to the heart muscle at distal electrode ends and extending through an incision in the patient's skin. To effect unipolar pacing of the heart, a single such implantable pacing lead was employed in conjunction with a subcutaneously implanted or skin-surface attached return electrode coupled to an external lead conductor. To effect bipolar pacing of the heart, two such implantable pacing leads were implanted with the electrode ends implanted a distance apart. The attachment of the proximal ends of the lead conductors to the temporary cardiac pacemaker connector elements was initially effected by simply stripping insulation from the proximal conductor ends, and inserting and securing the bare conductor ends in transverse openings in threaded posts. Later, finished connector pins were formed at the proximal connector ends of the lead bodies that could be inserted into the end openings of thumb nuts and connector posts.

Implantable pacing leads evolved into permanent, unipolar and bipolar, endocardial and epicardial, pacing leads for chronic implantation in a patient. The proximal electrical connector assemblies were then connected with connector elements of a totally implanted, cardiac pacemaker pulse generator. To withstand stress, implantable pacing lead conductors were formed of coiled wire and inserted within an insulative lead body lumen, thereby providing a coiled wire lumen that was sized to receive a stiffening stylet wire to assist tranvenous implantation of the endocardial pacing leads. The proximal end of the coiled wire conductor was attached to a tubular connector pin at the terminus of the lead connector and shaped to be received in the connector assembly of the implantable pacemaker pulse generator. In the case of endocardial permanent pacing leads, the connector or pin was formed with a lumen therein aligned with the coiled wire lumen so that the stiffening stylet wire could be inserted down the length of the lead body during the travenous introduction and withdrawn after placement of the distal electrode was achieved. Many of these features are employed in current permanent pacing leads.

More recently, bipolar and multi-polar permanently implantable pacing leads and leads for use in pacing and cardioversion/defibrillation (collectively referred to as permanent implantable cardiac leads) have been developed using coaxially arranged, coiled wire conductors and/or parallel-wound, multi-filar coiled wire conductors. In the case of endocardial cardiac leads, the stylet wire lumen is employed to receive the stiffening stylet wire for implantation as described above. The proximal connector end assemblies are formed with at least two spaced apart lead connector elements arranged in-line from a proximal lead connector pin to at least one or more distally located ring-shaped element or lead connector ring. Typical bipolar in-line lead connector assemblies for multi-filar, coiled wire conductors are shown, for example, in commonly assigned U.S. Pat. Nos. 4,944,088 and 4,951,687 and 5,007,435, respectively, the teachings of which are hereby incorporated by reference.

Unipolar and bipolar, temporary endocardial pacing leads and temporary epicardial heart wires were also developed for implantation of the distal electrode(s) thereof in contact with the endocardium or sutured through the epicardium of the hearts of hospitalized patients. The lead body size of these temporary pacing leads and heart wires has typically been smaller than that of permanent cardiac leads because of the absence of an internal wire coil lumen for receiving a stylet wire. Still, in the case of bipolar temporary pacing leads and heart wires, either a lead connector pin and ring set are employed providing a pair of lead connector pins.

During or after implantation of the implantable cardiac lead(s), an external pacing system analyzer (PSA), e.g. MEDTRONIC® Model No.'s 2290 and 8090, is attached to the proximal lead connector end assembly accessible through the incision to assess the performance of the system and verify proper lead placement. It is necessary in some cases to use either a disposable or a reusable "surgical cable" adaptor to complete the connection between the implanted lead and the external pacing system analyzer.

Some patient and surgical cable adaptors constitute a connector assembly at a first end that is compatible with the PSA or temporary pacemaker terminals, a cable including conductors extending from the first end to a second end, and lead connector element connectors at the second end. Typically, two to four conductors are included in the cable, and a set of two or four alligator clips are provided at the second end for attachment to one or more lead connector rings and a pin of one or two implantable cardiac leads.

In the case of a permanent pacing lead having a stylet wire fitted within the lead lumen and projecting out proximally through the connector pin, alligator clips are utilized that attach across the connector rings and pins. However, such an attachment is not as secure and electrically isolated as would be desirable. It is undesirable to either lose the connection or to allow an electrical static discharge or other shock or impulse to reach the heart through the exposed lead connector ends. Furthermore, it has been observed that the careless use of alligator clips can damage the insulation sheathes adjacent to the lead connector end ring or connector pins. This problem is further complicated in the case of leads having a plurality of contact rings separated by insulative sealing surfaces. That is, not only is there a potential for shorting between alligator clips and/or test probes, but such clips may cause damage to the insulation/sealing areas adjacent the contact rings.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description.

The present invention will hereinafter be described in conjunction with the appended drawings, wherein like numerals denote like elements, and:

FIG. 5 is an isometric view of the medical lead adaptor shown in FIG. 3A modified to accommodate a stylet wire and control knob;

DETAILED DESCRIPTION OF THE INVENTION

The following detailed description of the invention is merely exemplary in nature and is not intended to limit the scope, applicability, or configuration of the invention in any way. Rather, the following description provides a convenient illustration for implementing exemplary embodiments of the invention. Various changes to the described embodiments may be made in the function and arrangement of the elements described herein without departing from the scope of the invention.

The invention is described in connection with a number of embodiments of medical lead adaptor assemblies, each of which allows electrical coupling between the proximal lead connector end assembly of a cardiac or similar lead and an external medical device. The lead adaptor is capable of being coupled to external electrical conductors by means of conductive probes, clips, and the like. The inventive medical lead adaptor assembly may be configured to accept lead connectors that may or may not include a stylet wire or a guide wire passing therethrough. Furthermore, the inventive lead adaptor may be utilized in conjunction with leads having compatible lead connector element dimensions; i.e. compatible spacing between and diameters of ring contacts. Of course, the medical lead adaptor assembly in accordance with the present invention may be provided with different dimensions so as to accommodate a variety of cardiac or other types of leads.

Figure 1:
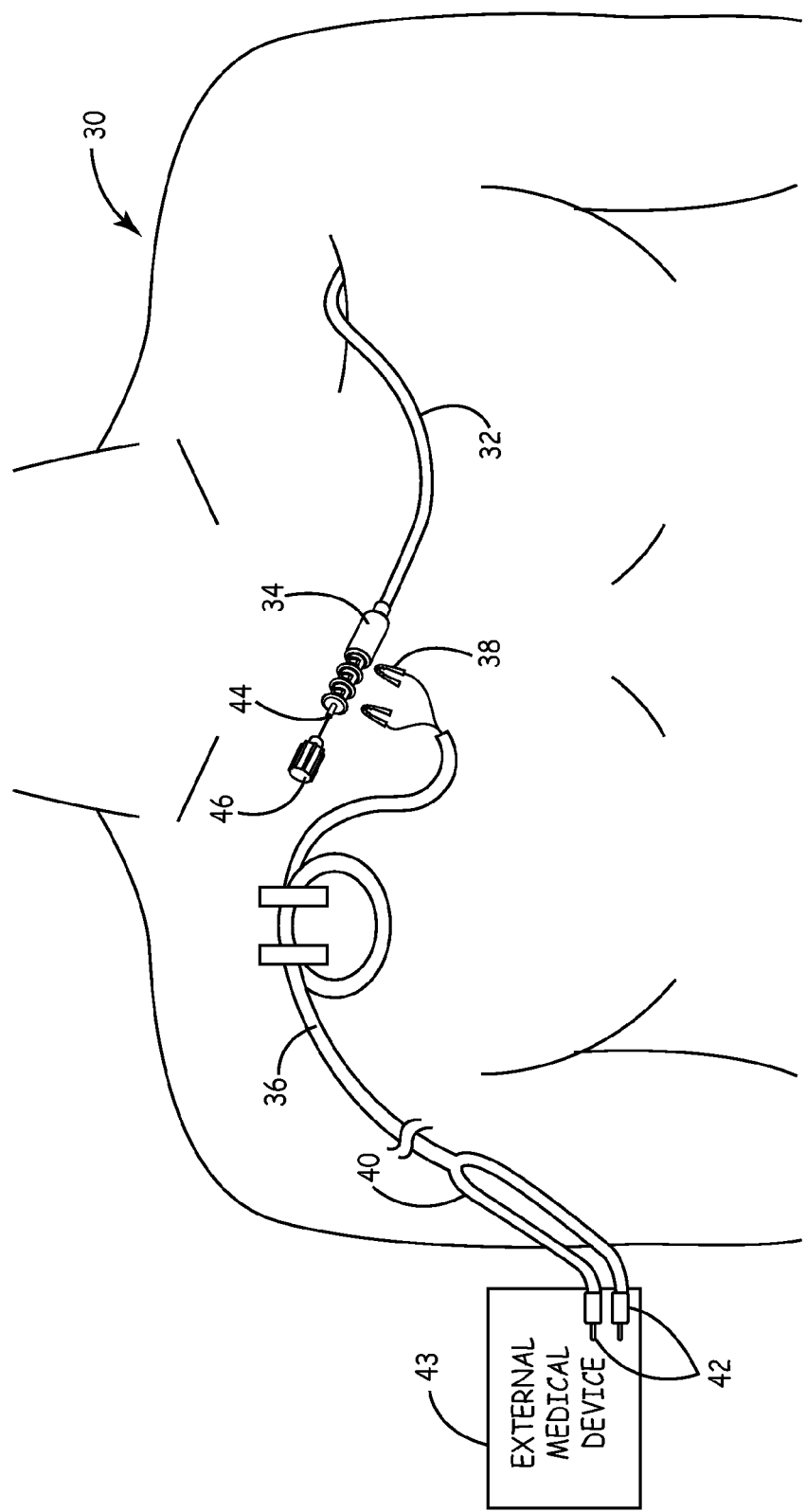
FIG. 1 is a simplified schematic view of a cardiac lead implanted in a patient and coupled to an external medical device by means of an inventive medical lead adaptor.

FIG. 1 is a simplified schematic view of a cardiac lead implanted in a patient and coupled to an external medical device by means of an inventive medical lead adaptor. As can be seen, a proximal portion of an implantable cardiac lead is shown in part and includes an elongated implantable lead body 32 extending from a lead adaptor assembly 34 toward the distal cardiac lead end (not shown). The distal cardiac lead end includes at least one electrode implanted in contact with a heart chamber of patient 30. The lead connector (shown in FIG. 2 as 50) is received within adaptor 34 as will be described hereinafter for providing rapid electrical connection between lead body 32 and external medical device 43 by means of a cable 36 and one or more contact elements, examples of which include alligator clips 38, as illustrated in FIG. 1, and probes. The proximal end 40 of cable 36 is provided with means for electrical connection to one or more external medical devices by means of, for example, connector 42 that engages connector terminals associated with the external medical device. The external medical device connection terminals may take any form, such as those associated with the above-referenced MEDTRONIC® Models 2290 and 8090 or Model 5348 and 5388 temporary pacemakers. A stylet wire 44 extends through connector assembly 50 and lead body 32; alternately an interventional guide wire may extend through connector assembly 50 and lead body 32. In this manner, stylet wire 44, or a guide wire, may be rotated, axially extended, withdrawn, etc., to aid in implantation of lead body 32.

Figure 2:
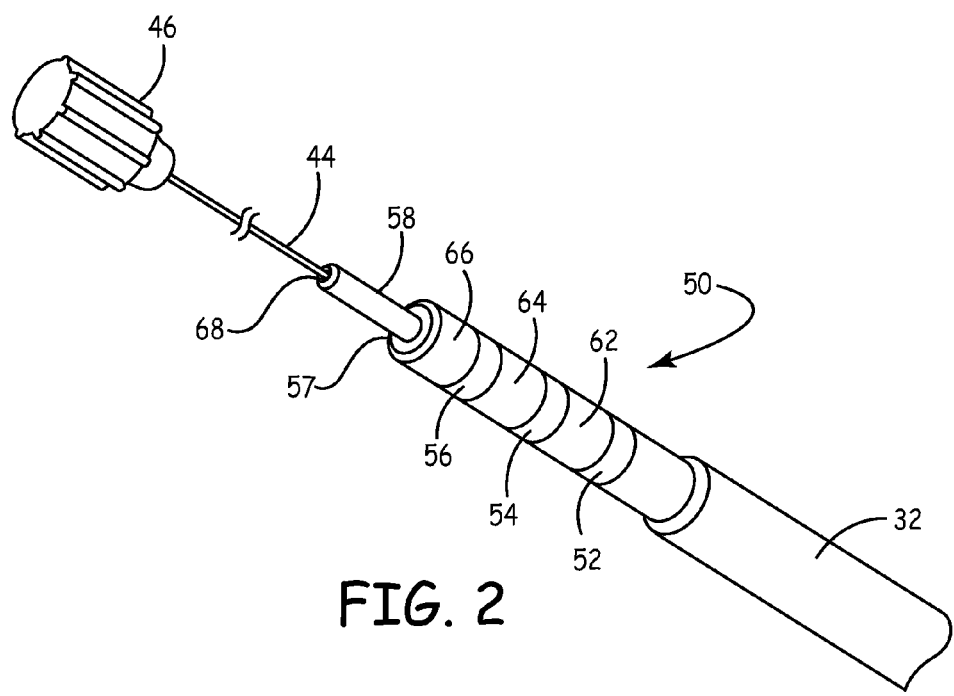
FIG. 2 is an isometric view of a lead connector assembly capable of being received into an inventive medical lead adaptor.

FIG. 2 is an isometric view of a lead connector assembly capable of being received into an adaptor according to the present invention, various embodiments of which are described herein. Connector 50 at the proximal end of lead body 32 includes contact rings 52, 54 and 56 and a pin contact 58, each electrically coupled to conductors within lead body 32 and electrically isolated from each other by insulative layers within lead body 32 and by sealing rings 62, 64, and 66. Extending from a lumen 68 in lead connector 50 is stylet wire 44 which may be manipulated by means of stylet knob 46 as described above. While connector 50 has been shown as comprising three contact rings and three insulative sealing rings, it should be clear that the inventive medical lead adaptor assembly is equally applicable to connectors having a different number of contact rings including a single contact ring as is typical of IS-1 connectors.

Figure 3A:
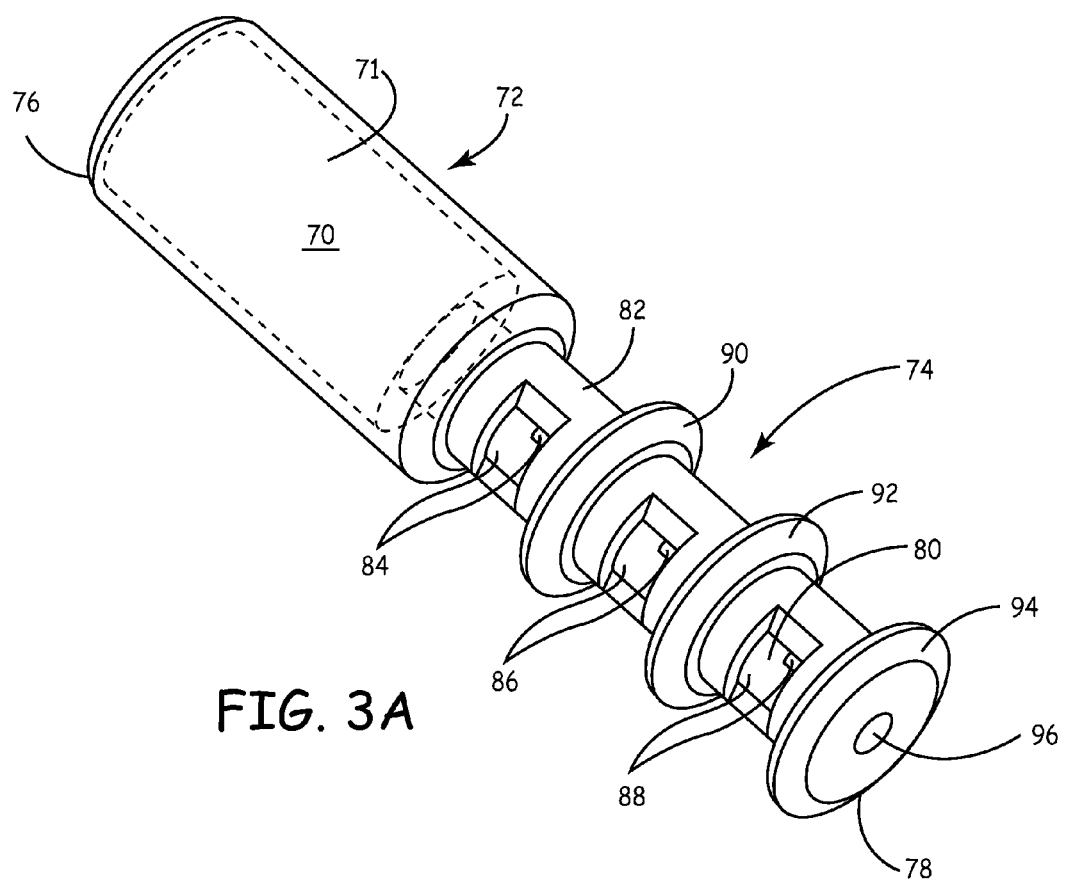
FIG. 3A is an isometric view of one embodiment of a medical lead adaptor according to the present invention.

FIG. 3A is an isometric view of an embodiment of the inventive medical lead adaptor assembly. Adaptor assembly 70, made of an insulative material, preferably a hard plastic, includes a grip portion 72 and a contact portion 74 through which a connector receptacle extends; the connector receptacle, configured to matingly engage connector 50 (FIG. 2) extends in a first part 71 (shown partially dotted) from an opening at a distal end 76 to contact portion 74 and in a second part 80 through contact portion 74 to a proximal end 78 where it joins with a proximal opening 96. Both grip portion 72 and contact portion 74 have a sidewall forming a generally curved outer surface (i.e. both sections are generally cylindrical).

As illustrated in FIG. 3A, contact portion 74 includes three pairs of diametrically opposed contact openings 84, 86, and 88 extending from an outer surface 82 into a second part of connector receptacle; contact openings 84, 86, and 88 are shown separated by spaced ridge portions 90, 92, and 94 extending radially outward from surface 82. According to alternate embodiments of the present invention, contact portion 74 includes any number of contact openings and may not include ridges.

Figure 3B:
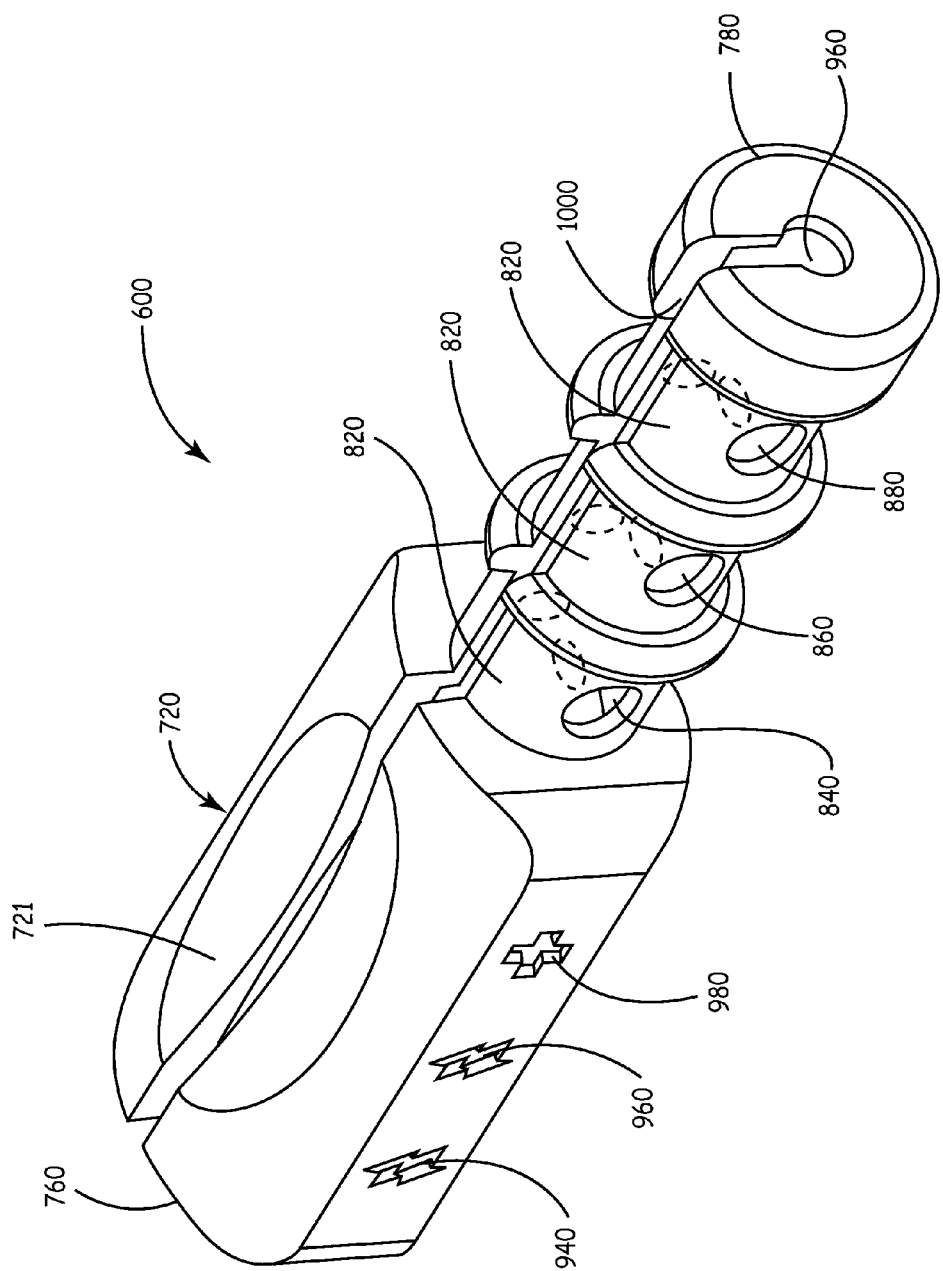
FIG. 3B is an isometric view of another embodiment of a medical lead adaptor according to the present invention.

FIG. 3B is an isometric view of another embodiment of a medical lead adaptor 600 according to the present invention. As illustrated in FIG. 3B, adaptor 600 includes a grip portion 720 formed having a generally ovular or elliptical section and including a recessed area 721 for enhanced gripping; grip portion 720 further includes labels 940, 960, and 980 corresponding to and identifying each contact opening, 840, 860, and 880 respectively. Contact openings 840, 860, and 880 may each be single openings, diametrically opposing pairs of openings (FIG. 3A), or a set of three openings aligned and spaced about a circumference of surfaces 820, as illustrated in FIG. 3B with dashed lines; the latter being compatible with an embodiment of a contact clip illustrated in FIG. 7C. Although FIG. 3B shows labels 940 and 960 as symbols representing high voltage and label 980 as a symbol representing a positive polarity or an anode, these symbols may be take on any form to identify contact openings according to any application; for example each contact opening may correspond with a low voltage contacts of either polarity. Furthermore, although symbols 940, 960, and 980 are shown as cut outs through grip 720, symbols may be formed in any manner, molded, cut, printed, or pasted, on grip 720. FIG. 3B further illustrates adaptor 600 including an elongated slot 1000 extending from a distal end 760 to a proximal end 780. Slot 1000 corresponds with a slot 100 illustrated in FIG. 5 and will be described in greater detail in conjunction with FIG. 5.

Figure 4A:
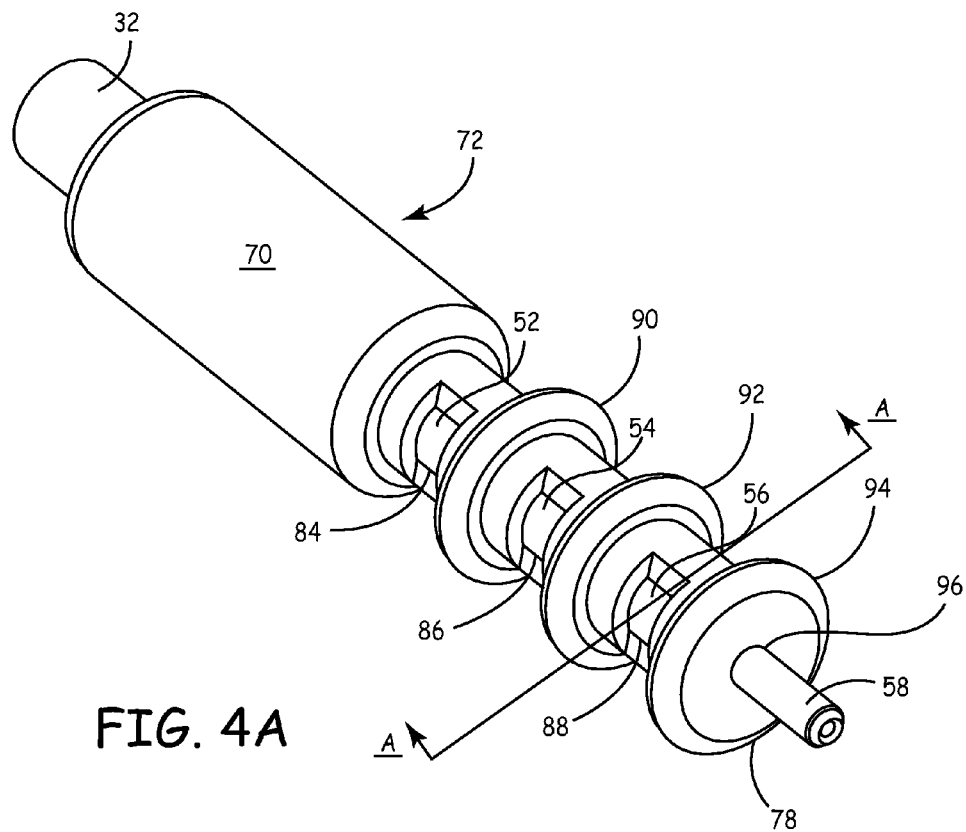
FIG. 4A is an isometric view of the medical lead adaptor shown in FIG. 3A having a lead connector assembly (FIG. 2) positioned therein.

FIG. 4A is an isometric view of a lead connector engaged within the medical lead adaptor assembly shown in FIG. 3A. Connector 50 has been inserted into adaptor 70 at distal end 76 until pin contact 58 protrudes through proximal opening 96. As illustrated in FIG. 4A, according to embodiments of the present inventions, when a connector, such as connector 50 illustrated in FIG. 2, is properly engaged within adaptor 70, ring contacts 52, 54, and 56 reside adjacent to and are accessible through contact openings 84, 86, and 88 respectively, and pin contact 58 protrudes through opening 96. Thus, ring contacts 52, 54, and 56 and pin contact 58 are exposed and may be contacted by contact elements, for example alligator clips 38 (FIG. 1), so as to electrically couple lead body 32 to external medical device 43 (FIG. 1). The longitudinal width of the contact openings 84, 86, and 88 corresponds to widths of ring contacts 52, 54, and 56 (FIG. 2) being approximately less than or equal to the widths of the ring contacts so as to prevent a contact element, such as alligator clips 38, from touching adjacent sealing rings 62, 64, and 66 (FIG. 2). Therefore, sealing rings 63, 64, and 66 remain protected within adapter 70. To achieve proper placement and retention of connector 50 within adaptor 70, surface 57 abuts an interior surface of second part of connector receptacle 80 at proximal end 78 when connector 50 is fully inserted within adaptor 70. Furthermore, according to embodiments of the present invention, first part of connector receptacle 71 has a diameter sized to create a press fit about a portion of connector 50 residing in first part 71 when connector 50 is fully inserted into adaptor; alternately or additionally second part of connector receptacle 80 has a diameter sized to create a press fit about a second portion of connector 50 residing in second part 80 when connector 50 is fully inserted.

Figure 4B:
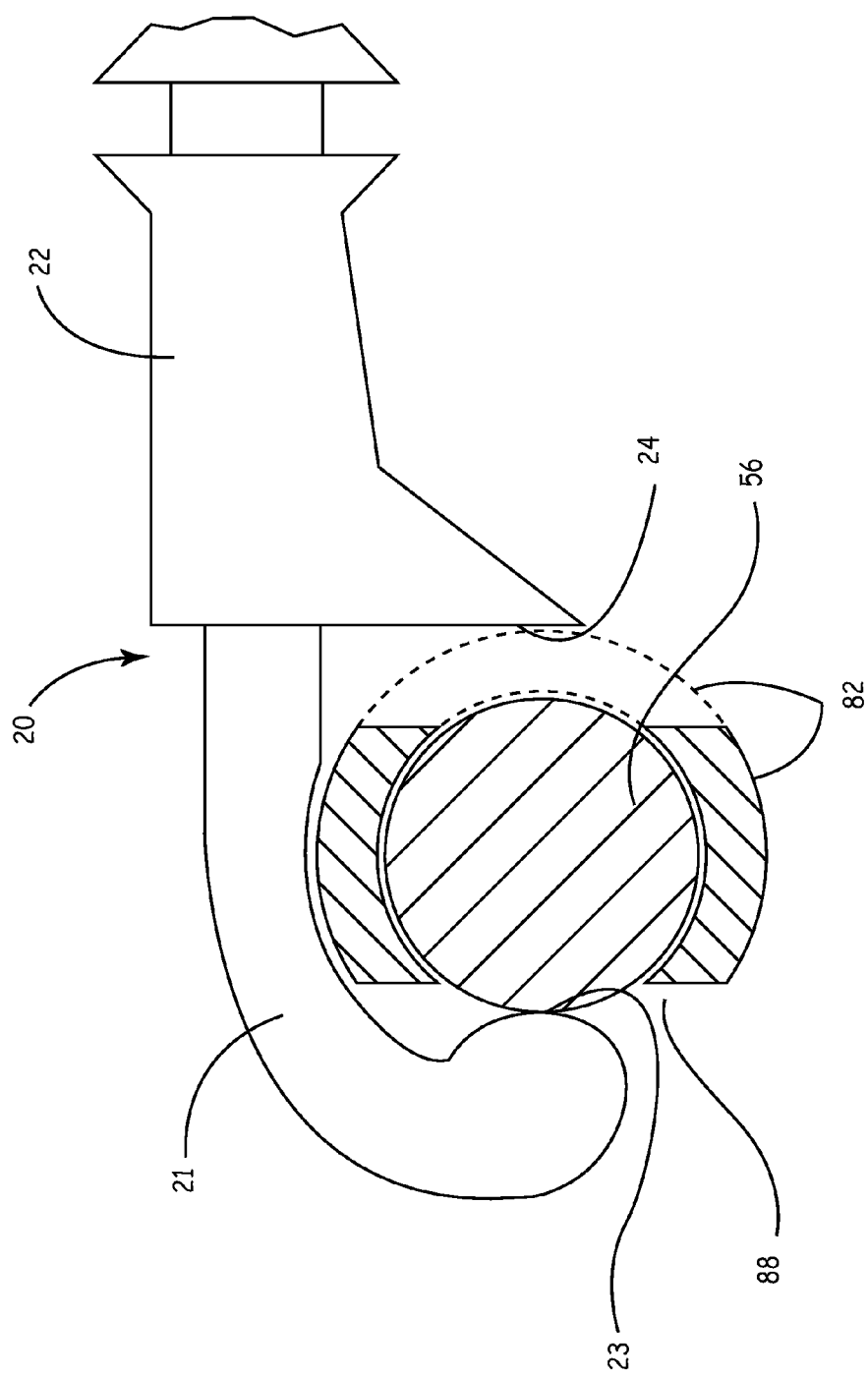
FIG. 4B is a radial section view through section line A—A of FIG. 4A.

FIG. 4B is a radial section view through section line A—A of FIG. 4A. FIG. 4B illustrates a probe 20 electrically engaging ring contact 56 of connector 50 through contact opening 88; dashed lines indicate an extension of outer surface 82 according to an alternate embodiment wherein opening 88 is singular rather than paired as was previously described in conjunction with FIG. 3A. Probe 20, a type well known to those skilled in the art, includes an electrical contact portion 21 and an insulative sheath 22 through which contact portion extends; spring loading of probe 20 secures ring contact 56 and outer surface 82 between a contact surface 23 and an opposing face 24 of insulative sheath.

FIG. 5 is an isometric view of the medical lead adaptor shown in FIG. 3A modified to accommodate a stylet wire and control knob. According to embodiments of the present invention FIG. 5 illustrates adaptor 70 including a longitudinal slot 100 extending through the sidewall of both grip portion 72 and contact portion 74; a width of slot is between approximately 0.010 inch and approximately 0.018 inch, accommodating stylet wires such as wire 44 and standard interventional guide wires that may be used to implant leads. After stylet wire 44 is passed through slot 100 into the connector receptacle, connector 50 may be inserted as described above, so that pin contact 58 and stylet wire 44 exit adaptor 70 through opening 96.

Figure 6:
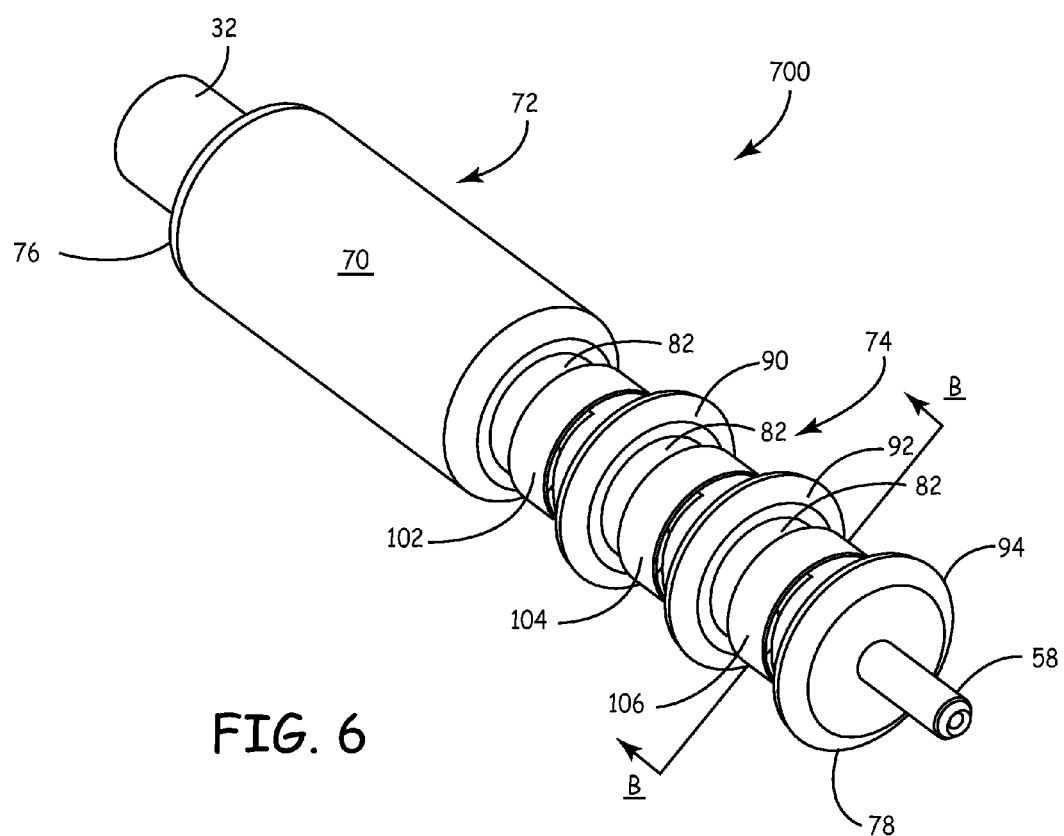
FIG. 6 is an isometric view of the inventive medical lead adaptor shown in FIG. 3A equipped with external contact clips.
Figure 7A:
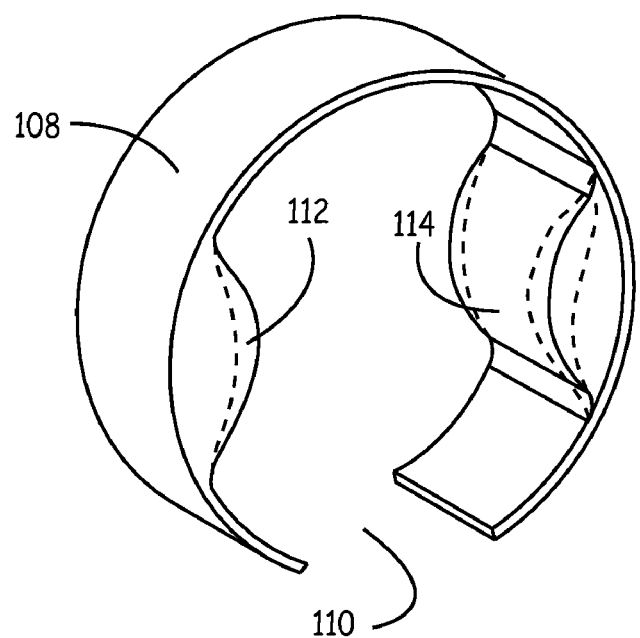
FIG. 7A is an isometric view of a contact clip shown in FIG. 6.
Figure 7B:
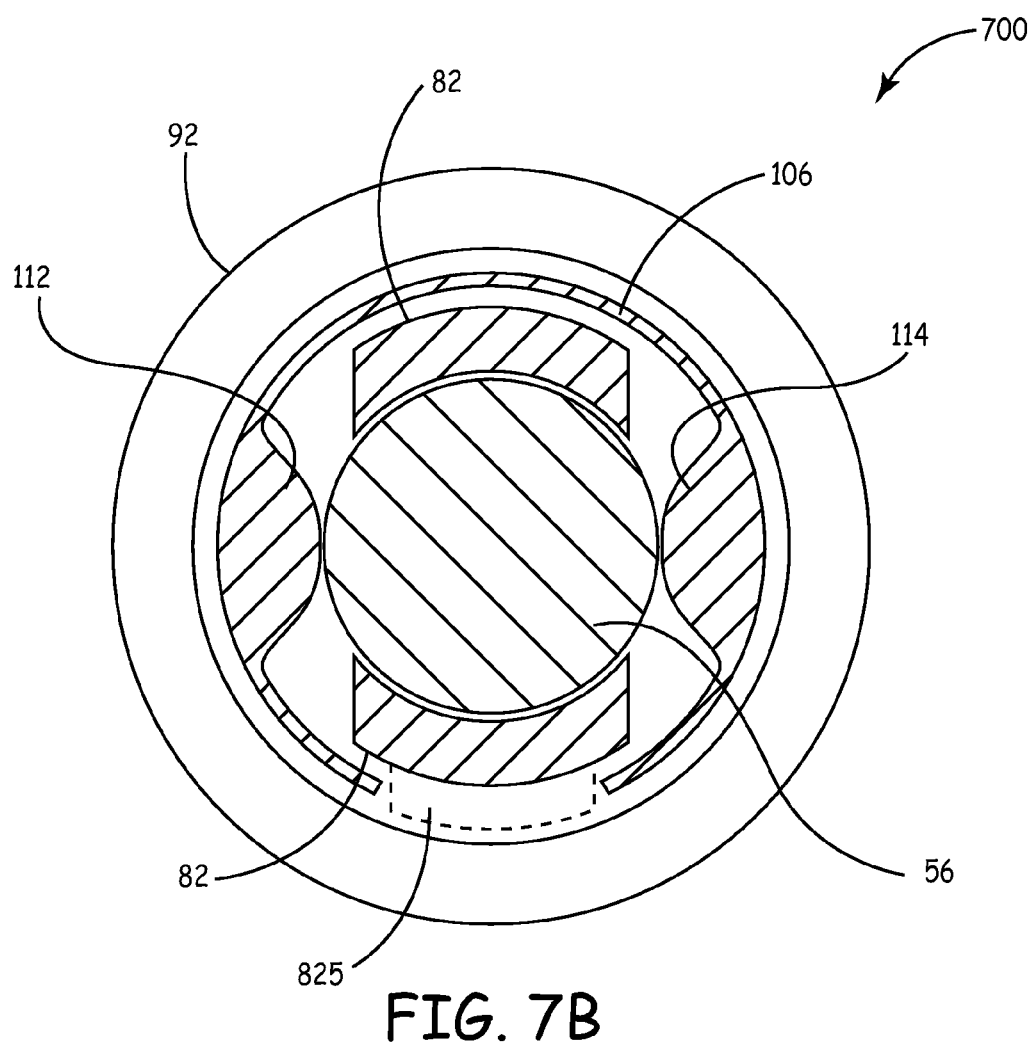
FIG. 7B is a radial section view through section line B—B of FIG. 6.

In some situations, it may be desirable to provide a larger contact area to facilitate electrical connection between the contact rings 52, 54, and 56 (FIG. 2) and connector elements, such as alligator clips 38, of external medical device 43 (FIG. 1). This may be accomplished as shown in FIG. 6 and FIG. 7A–B. FIG. 6 is an isometric view of a medical lead adapter assembly 700 according to another embodiment of the present invention. As illustrated in FIG. 6, adapter assembly 700 incorporates adaptor 70, shown in FIG. 3, equipped with external contact clips 102, 104, and 106. Contact clips 102, 104, and 106 are positioned around a substantial portion of the periphery of outer surface 82 of adapter 70 proximate contact apertures 84, 86, and 88 (FIG. 3).

Figure 8:
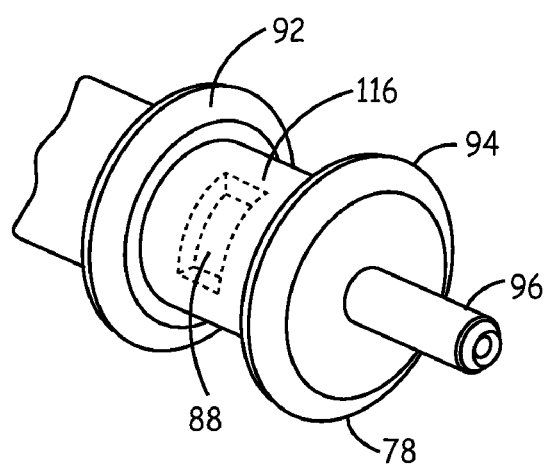
FIG. 8 is an additional isometric view of the inventive medical lead adaptor equipped with a wider contact clip.

FIG. 7A is an isometric view of one such contact clip and FIG. 7B is a radial section view through section line B—B of FIG. 6. As illustrated in FIG. 7A, according to one embodiment of the present invention, each contact clip includes an outer portion having a generally curved outer contact surface 108, a slot of discontinuity 110 to permit resilient placement of contact clip (e.g. 102) over surface 82, and protrusions 112 and 114 which are designed to extend through diametrically opposed contact openings (e.g. 88 in FIG. 3) and make electrical contact with an associated contact ring of a lead connector. FIG. 7B illustrates protrusions 112 and 114 of contact clip 106 contacting ring contact 56, being held firmly against ring 56 by means of a spring force. Contact clips 102, 104, and 106 may be pre-loaded, or opened slightly from a relaxed state, on surfaces 82 of adaptor 700 by means of a protrusion 825 from surfaces 82, shown by a dashed line, intervening in slot 110. According to some embodiments of the present invention protrusions 112 and 114 of contact clips 102, 104, 106 further include chamfered edges illustrated by dashed lines in FIG. 7A; these chamfered edges facilitate insertion of a lead connector, such as connector 50 (FIG. 2), into adaptor assembly 700 by providing an enlarged entry into clips 102, 104, 106 and thus enabling connector 50 to spread open clips 102, 104, 106. Contact clips 102, 104, 106 may be made of any material having an appropriate resiliency and electrical conductivity, examples of which include stainless steel and platinum-iridium alloys. While clip 102 has been shown and described as having two substantially diametrically opposed protrusions 112 and 114, it should be clear that just one or a larger number of protrusions may be employed depending, in part, on the number and configuration of the contact openings in lead adaptor assembly 70. Furthermore, while clips 102, 104, and 106 are shown as having relatively narrow contact surfaces (e.g. 108), wider contact surfaces (e.g. extending from ridge-to-ridge) could be utilized. Thus, the contact surface may be wider than the width of its associated contact aperture as is shown in FIG. 8 where 116 indicates a contact clip extending from ridge 92 to ridge 94 and wherein contact aperture is indicated by dashed lines.

Figure 7C:
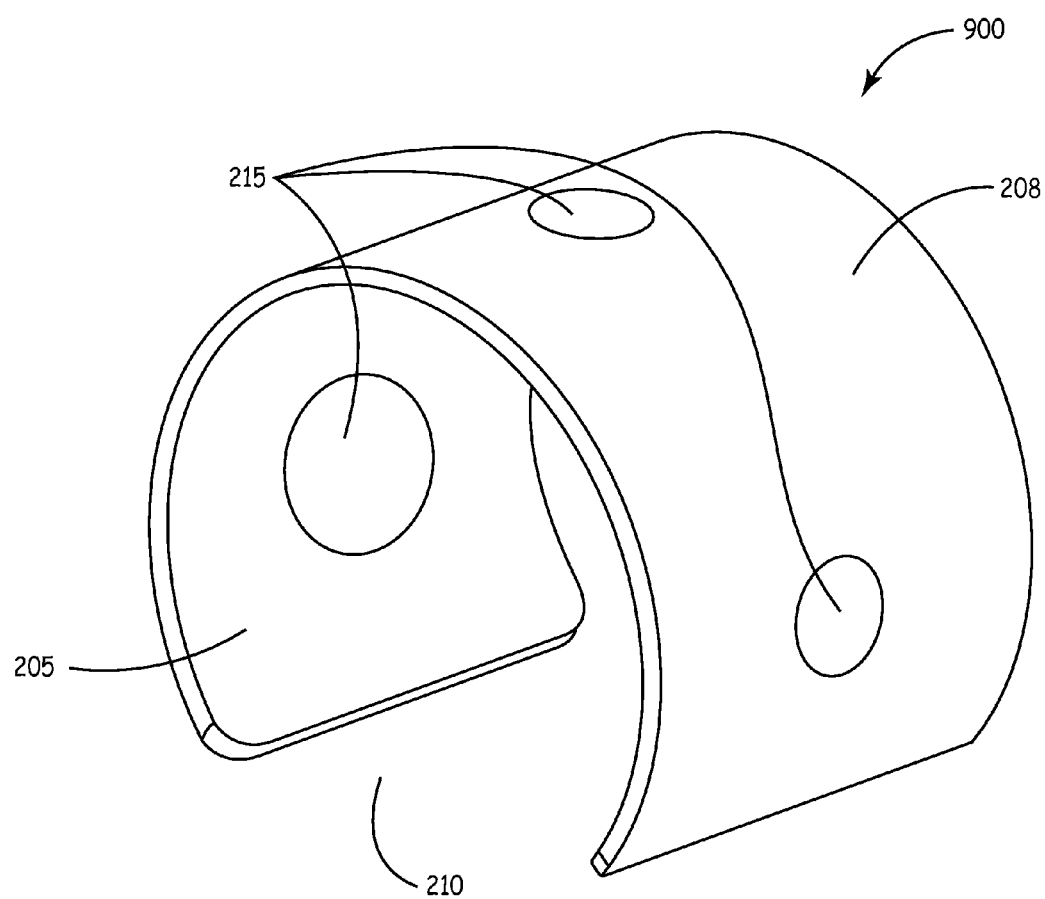
FIG. 7C is an isometric view of an alternative embodiment of a contact clip according to the present invention.

FIG. 7C is an isometric view of an alternative embodiment of a contact clip 200 according to the present invention. FIG. 7C illustrates clip 200 including contact surfaces formed by dimples 215 depressed from an outer surface 208 and protruding from an inner surface 205 in order to make electrical contact with a ring of a connector inserted within an adaptor having apertures corresponding with dimples 215, for example adaptor 600 illustrated in FIG. 3B. Clip 200 includes a slot of discontinuity 210 to permit resilient placement of contact clip 200 over a surface of an adaptor, such as the adaptor illustrated in FIG. 3B, in a manner similar to that described for clips 102, 104, and 106 in conjunction with FIGS. 6 and 7B.

Figure 9:
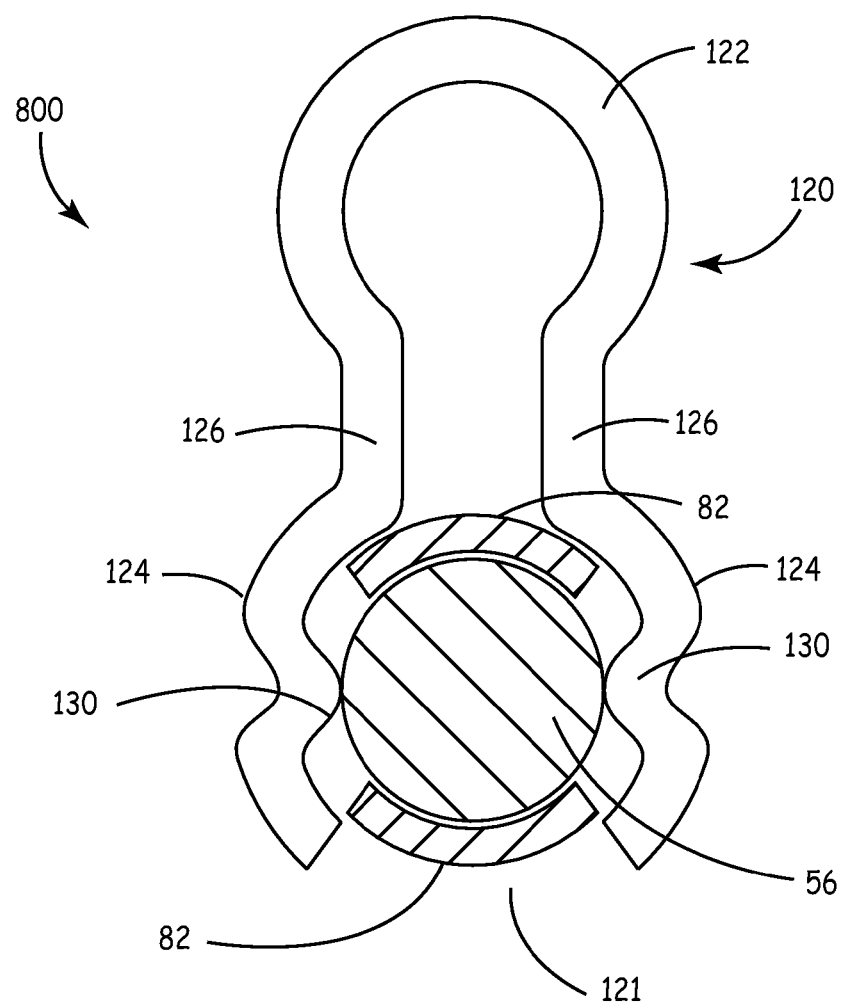
FIG. 9 is a radial section view of a medical lead adapter assembly according to yet another embodiment of the present invention.
Figure 10:
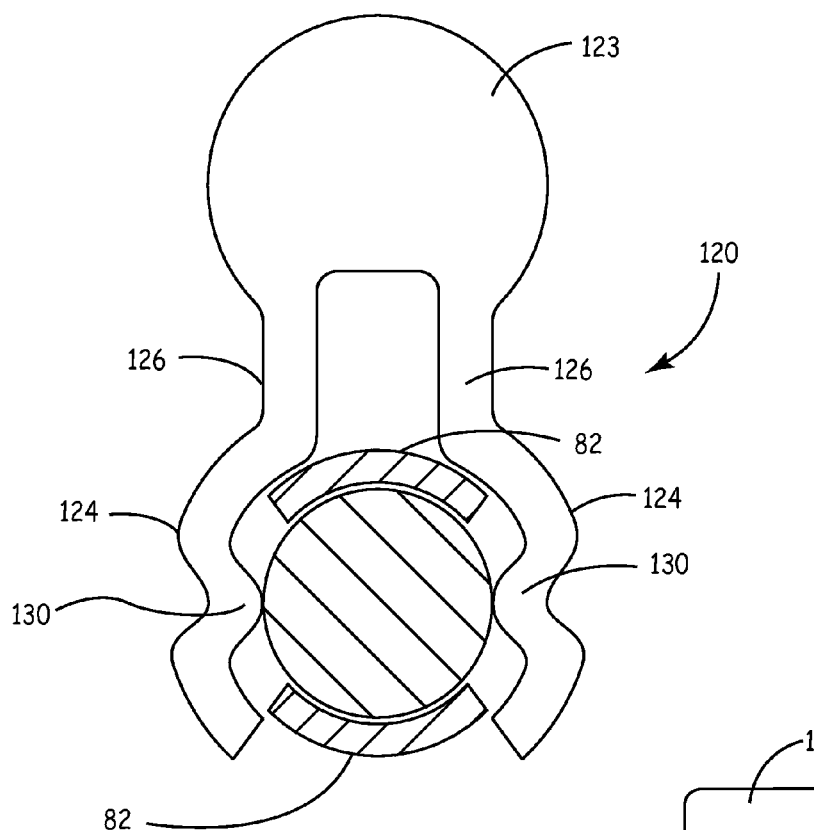
FIG. 10 and FIG. 11 are plan and side views respectively of two forms of contact clips suitable for use with embodiments of a medical lead adaptor assembly according to the present invention.
Figure 11:
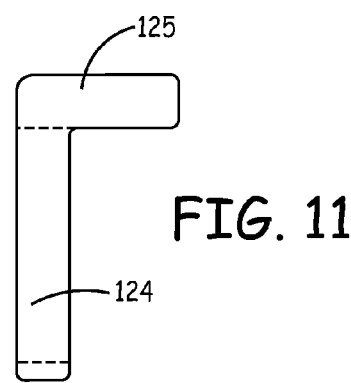

FIG. 9 is a radial section view of a medical lead adapter assembly 800 according to yet another embodiment of the present invention. FIG. 9 illustrates assembly 800 in a section taken through line B—B shown in FIG. 6 for assembly 700 wherein clips 102, 104, 106 are replaced with an alternate embodiment of a contact clip 120. Referring to FIG. 9, clip 120 includes a loop contact portion 122 joined via connecting segments 126 to ring contact segments 124 and a slot of discontinuity 121 to permit resilient placement of clip 120 over surface 82 of adaptor 70. A pair of internally directed protrusions 130 is designed to extend through diametrically opposed contact openings (e.g. 88 in FIG. 3) and make electrical contact with an associated contact ring of a lead connector, such as contact ring 56. Clip 120 may be formed from a conductive wire or sheet made of any material having an appropriate resiliency and electrical conductivity, examples of which include stainless steel and platinum-iridium alloys. As previously described for adaptor assembly 700, according to one embodiment, a lead connector, for example connector 50, spreads clip 120 as connector passes into assembly 800; alternately clip 120 may be assembled onto adaptor 70 after lead is positioned within the connector receptacle thereof. Contact to an external medical device may be accomplished by attaching clips, such as alligator clips 38 (FIG. 1), to loop contact portion 122 of clip 120. It should be clear that loop contact portion 122 may take on an alternate geometry, for example, a substantially flat contact tab 123 as is shown in FIG. 10, or an angled tab 125 (e.g. 90 degrees with respect to ring contact segments 124) as is shown in the side view of FIG. 11.

Figure 12A:
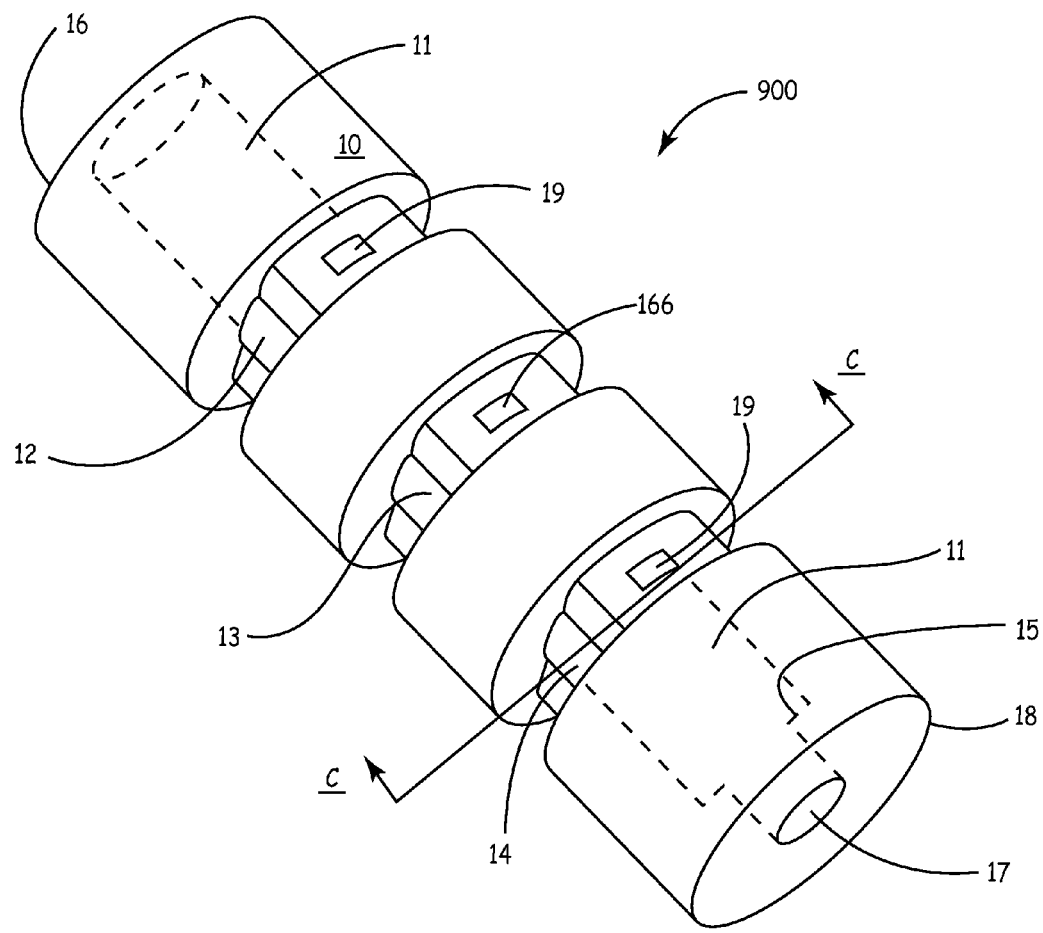
FIG. 12A is an isometric view of a medical lead adaptor assembly according to yet another embodiment of the present invention.
Figure 12B:
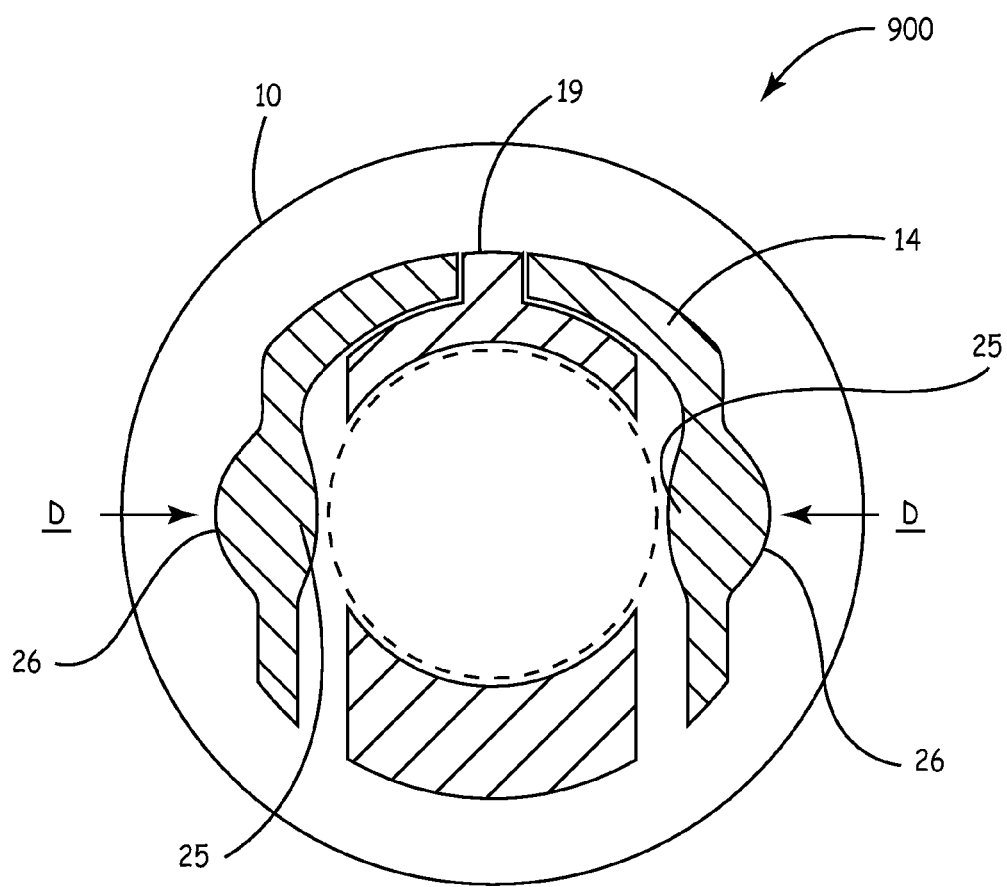
FIG. 12B is a radial section view through section line C—C of FIG. 12A.

FIG. 12A is an isometric view of a medical lead adaptor assembly 900 according to yet another embodiment of the present invention, and FIG. 12B is a radial section view through section line C—C of FIG. 12A. FIG. 12A illustrates adaptor assembly 900 including a sleeve 10 carrying contact clips 12, 13, and 14; sleeve 10, made of an insulative material, preferably a hard plastic, includes an open distal end 16, a proximal end 18, and a connector receptacle 11 (shown by dashed lines in proximity to distal and proximal ends) extending through sleeve 10 from the distal end to an opening 17 at proximal end 18. A lead connector, for example connector 50 illustrated in FIG. 2, is inserted into distal end 16 until surface 57 of connector 50 abuts an interior surface 15 and pin contact 58 protrudes through opening 17 in a manner similar to that illustrated in FIGS. 4A and 6. When connector is fully inserted, ring contacts 52, 54, are 56 are positioned within sleeve 10 for electrical engagement with contact clips 12, 13, and 14 respectively. Contact clips 12, 13, 14 are mounted on sleeve 10, for example, as illustrated in FIGS. 12A–B, by being fitted over nubs 19. According to some embodiments of the present invention, as illustrated in FIG. 12B, clips 12, 13, 14 are formed such that internal contact surfaces 25 are spread apart to allow free passage of a lead connector, such as connector 50 (FIG. 2), into assembly 900. Arrows D represent a force of a contact element, for example alligator clips 38 associated with external device 43 (FIG. 1), on external surfaces 26 of contact clip 14, which will bring internal contact surfaces 25 into electrical contact with a ring contact (shown with dashed lines) of a lead connector, for example ring contact 56 of connector 50 (FIG. 2), that has been inserted within assembly 900.

Figure 13:
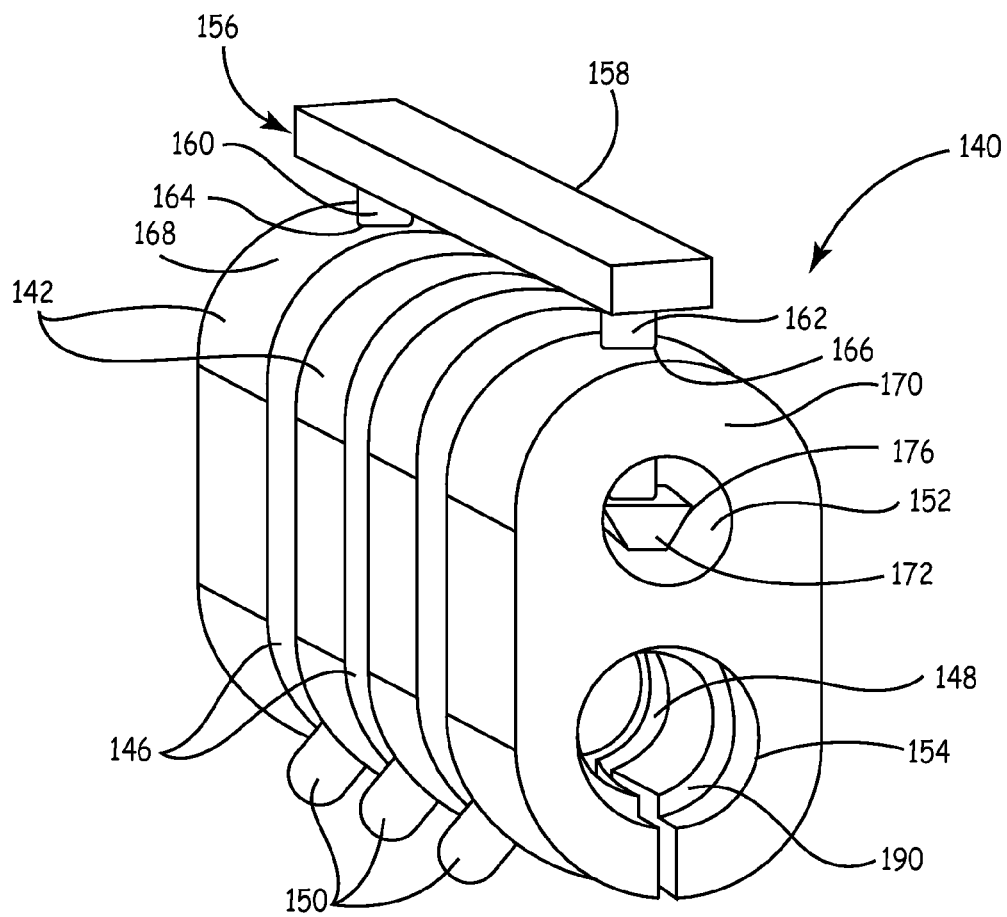
FIG. 13 and FIG. 14 are isometric and front views respectively of a medical lead adaptor assembly according to yet another embodiment of the present invention.
Figure 14:
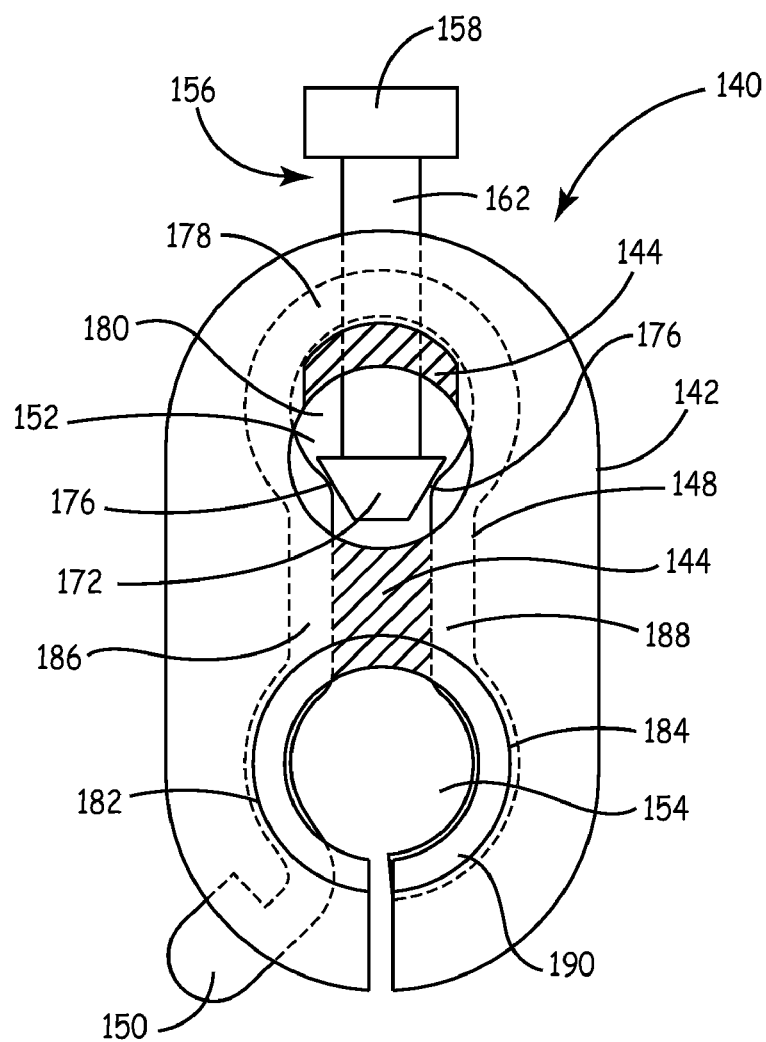
Figure 15:
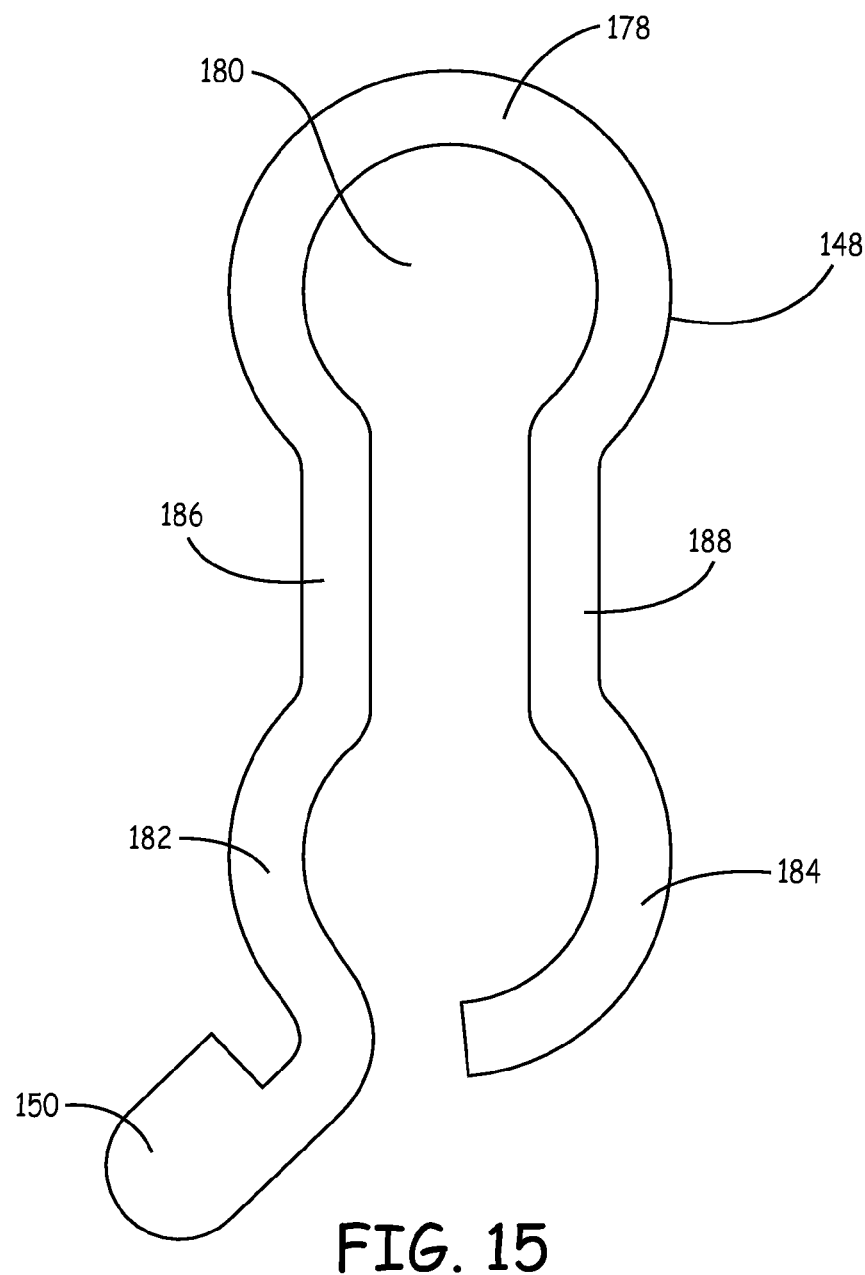
FIG. 15 is a plan view of a clip for use in conjunction with the medical lead adaptor assembly shown in FIG. 13 and FIG. 14.

FIG. 13 and FIG. 14 are isometric and front views respectively of yet another embodiment of a medical lead adaptor assembly, and FIG. 15 is a plan view of a clip for use in conjunction with the adaptor assembly shown in FIG. 13 and FIG. 14. As illustrated in FIGS. 13 and 14, a medical lead adaptor assembly 140 includes of a plurality (e.g. four) body segments 142 fixedly coupled together by an internal connecting member 144. Segments 142 and connecting members 144 are preferably integrally formed and made of an insulative material as was the case with the adapter shown in FIG. 3. Segments 142 are spaced so as to define a plurality of clip retaining slots 146 therebetween. A clip 148 of the type shown in FIG. 15 is positioned on internal connecting member 144 within each of slots 146 such that connecting tabs 150 extend through slots 146 for potential electrical coupling to contact elements, for example alligator clips 38 associated with external device 43 (FIG. 1).

First and second longitudinal lumens 152 and 154 extend through lead adapter 140. Lumen 152 is preferably positioned substantially directly above lumen 154 as shown in FIG. 14. A push bar assembly 156 comprises a longitudinal push bar 158 fixedly coupled at its ends to coupling members or struts 160 and 162. As can be seen, struts 160 and 162 extend into lumen 152 via opening 164 and 166 respectively. Struts 160 and 162 fixedly engage an actuating bar 172 longitudinally housed within lumen 152 that has a generally trapezoidal cross-section having upwardly and outwardly extending inclined surfaces 176.

Referring to FIG. 15, clip 48 includes a generally circular portion 178 defining an opening 180 therethrough and curved ring-contact segments 182 and 184, which are coupled to circular portion 178 by connecting segments 186 and 188 respectively. For this purpose, clip 148 is preferably formed as a unitary, integral structure. As can be seen, generally flattened contact tab 150 is integrally formed as an extension of ring contact segment 182.

Referring again to FIGS. 14 and 15, it can be seen that clips 148 are positioned in slots 146 such that actuating bar 172 passes through openings 180 in clips 148, and inclined surfaces 176 reside adjacent the junctions of circular portion 178 and connecting segments 186 and 188. Pressing push-bar 158 will cause actuating bar 172 to abutingly engage connecting segments 186 and 188 causing them to spread apart which in turn causes ring contact segments 182 and 184 to likewise spread apart. In this condition, connector 50 (FIG. 2) may be inserted into lumen 154 until lead body 32 (FIG. 2) abuts raised surface 190 thereby properly positioning the ring contacts on connector 50 adjacent contact segments 182 and 184 of clips 148. Releasing push-bar 158 permits ring contact segments 182 and 184 to return to their original position gripping and electrically contacting their respective contact ring on connector 50 so as to provide the desired electrical connection thus permitting electrical connection to external medical device 43 as previously described. To remove connector 50, it is only necessary to press push-bar 158. Ring contact segments 182 and 184 disengage from connector 50, and connector 50 may be withdrawn. While clips 148 and actuating member 172 have been described in terms of specific shapes, it should be understood that other shapes that perform the desired function of contacting and releasing connector 50 might be utilized.

Thus, there has been provided a number of embodiments of medical lead adaptor assemblies, each of which provides a means for electrical coupling between a connector assembly of a cardiac or similar lead with an external medical device wherein sealing zones of the lead connector assembly are protected from contact with conductive probes, clips and the like associated with the external medical device. The inventive medical lead adaptor assembly may be configured to accept lead connectors that may or may not utilize a stylet wire or a guide wire. Furthermore, the inventive lead adaptor may be utilized in conjunction with lead and wires that have compatible lead connector element dimensions; i.e. compatible assemblies in accordance with the present invention may be provided with different dimensions so as to accommodate a variety of cardiac or other types of leads.

While specific embodiments have been presented in the foregoing detailed description of the invention, it should be clear that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road-map for implementing an exemplary embodiment of the invention. It should be understood that various changes may be made in the function and arrangement of elements described in an exemplary embodiments without departing from the scope of the invention as set forth in the appended claims.

The invention claimed is:

1. An adaptor facilitating an electrical connection between an implantable medical lead connector and an external medical device comprising:
   a housing including a sidewall and a longitudinally extending connector receptacle;
   at least one contact opening passing through the sidewall to the receptacle and positioned in a location corresponding with at least one ring contact of the lead connector when the lead connector is engaged within the receptacle, the contact opening allowing electrical connection between at least one contact element of the external medical device and the at least one ring contact of the lead connector; and
   at least one contact clip positioned about the housing and including an external contact surface and an internal contact surface;
   wherein the internal contact surface extends through the at least one contact opening to electrically engage the at least one ring contact of the lead connector engaged within the receptacle of the adaptor housing; and
   the external contact surface provides an area for connection with the at least one contact element of the external medical device.

2. The adaptor of claim 1, wherein the at least one contact clip is preloaded by the housing.

3. The adaptor of claim 1, wherein the external contact surface forms a generally curved surface generally conforming to the sidewall of the housing.

4. The adaptor of claim 1, wherein the internal contact surface includes chamfered edges facilitating insertion of the connector therethrough.

5. The adaptor of claim 1, wherein the external contact surface forms a loop extending outward from the sidewall of the housing.

6. The adaptor of claim 1, wherein the external contact surface forms a substantially flattened tab extending outward from the sidewall of the housing.

7. The adaptor of claim 1, wherein the external contact surface includes a first longitudinal width and the contact opening includes a second longitudinal width, the first longitudinal width being greater than the second longitudinal width.

8. The adaptor of claim 1, further comprising a push-bar assembly;
   wherein the contact clip further includes a first segment, a second segment, and connecting segments joining the first segment and the second segment, the internal contact surface formed by the second segment and the external contact surface extending from the second segment; and
   the push-bar assembly operatively coupled to the contact clip, engaging the connecting segments from within the first segment to force apart the internal contact surface of the second segment out from the at least one contact opening, thus facilitating insertion of the lead connector through the housing.

9. The adaptor of claim 8, wherein the external contact surface is a substantially flattened tab.

10. An adaptor facilitating an electrical connection between an implantable medical lead connector and an external medical device comprising:
    a housing including a sidewall and a longitudinally extending connector receptacle;
    at least one contact opening passing through the sidewall to the receptacle and positioned in a location corresponding with at least one ring contact of the lead connector when the lead connector is engaged within the receptacle, the contact opening allowing electrical connection between at least one contact element of the external medical device and the at least one ring contact of the lead connector; and
    a contact clip fixedly mounted on the housing and including an external contact surface and an internal contact surface;
    wherein the internal contact surface is positioned in proximity to the at least one contact opening;
    the external contact surface provides an area for connection with the at least one contact element of the external medical device; and
    when the contact element of the external medical device connects with the external contact surface, the internal contact surface is forced through the contact opening to electrically engage the at least one ring contact of the lead connector engaged within the receptacle of the adaptor housing.

11. An adaptor facilitating an electrical connection between an implantable medical lead connector and an external medical device comprising:
   a housing including a sidewall and a longitudinally extending connector receptacle; and
   at least one contact opening passing through the sidewall to the receptacle and positioned in a location corresponding with at least one ring contact of the lead connector when the lead connector is engaged within the receptacle, the contact opening allowing electrical connection between at least one contact element of the external medical device and the at least one ring contact of the lead connector;
   wherein the housing further includes a distal end, a proximal end, and a slot extending longitudinally from the distal end to the proximal end and passing through the sidewall to the receptacle.

12. An adaptor facilitating an electrical connection between an implantable medical lead connector and an external medical device comprising:
   a housing including a sidewall and a longitudinally extending connector receptacle; and
   at least one contact opening passing through the sidewall to the receptacle and positioned in a location corresponding with at least one ring contact of the lead connector when the lead connector is engaged within the receptacle, the contact opening allowing electrical connection between at least one contact element of the external medical device and the at least one ring contact of the lead connector;
   wherein the at least one contact opening is defined by a diametrically opposing pair of openings.

13. The adaptor of claim 12, wherein the housing further includes a grip portion.

14. The adaptor of claim 12, wherein the housing further includes at least one pair of ridges extending outward from the sidewall of the housing and positioned on either side of the at least one contact opening.

15. The adaptor of claim 1, wherein the at least one contact opening is defined by three openings aligned and spaced about a circumference of the sidewall.

16. The adaptor of claim 12, wherein the connector receptacle includes a portion forming a press fit about a corresponding portion of the lead connector when the lead connector is engaged within the receptacle.

17. An adaptor facilitating an electrical connection between an implantable medical lead connector and an external medical device comprising:
   a housing including a sidewall and a longitudinally extending connector receptacle; and
   a plurality of openings passing through the sidewall to the receptacle and positioned in locations corresponding with a plurality of ring contacts of the lead connector when the lead connector is engaged within the receptacle; and
   a plurality of contact clips positioned about the housing, each of the plurality of clips including an external contact surface and an internal contact surface;
   wherein each internal contact surface, extending through each of the plurality of contact openings to electrically engage each of the plurality of ring contacts of the lead connector engaged within the receptacle of the adaptor housing, includes chamfered edges facilitating insertion of the connector therethrough; and
   each external contact surface provides an area for connection with each of a plurality of contact elements of the external medical device.

18. The adaptor of claim 17, wherein the housing further includes at least one pair of ridges extending outward from the sidewall of the housing and positioned on either side of the at least one contact opening.

19. The adaptor of claim 17, wherein the housing further includes a distal end, a proximal end, and a slot extending longitudinally from the distal end to the proximal end and passing through the sidewall to the receptacle.

20. The adaptor of claim 17, wherein each of the plurality of contact openings is defined by a diametrically opposing pair of openings.

21. The adaptor of claim 17, wherein the at least one contact opening is defined by three openings aligned and spaced about a circumference of the sidewall.

22. The adaptor of claim 17, wherein the connector receptacle includes a portion forming a press fit about a corresponding portion of the read connector when the lead connector is engaged within the receptacle.

23. The adaptor of claim 17, further comprising a push-bar assembly;
   wherein each of the plurality of contact clips further includes a first segment, a second segment, and connecting segments joining the first segment and the second segment, each internal contact surface formed by each of the second segments and each external contact surface extending from each of the second segment; and
   the push-bar assembly operatively coupled to the plurality of contact clips, engaging the connecting segments from within each of the first segments to force apart each of the internal contact surfaces of each of the second segments out from the each of the plurality of contact openings, thus facilitating insertion of the lead connector Through the housing.

* * * * *

UNITED STATES PATENT AND TRADEMARK OFFICE
CERTIFICATE OF CORRECTION

| | |
|---|---|
| PATENT NO. | : 7,130,699 B2 |
| APPLICATION NO. | : 10/436776 |
| DATED | : May 13, 2003 |
| INVENTOR(S) | : Huff et al. |

Page 1 of 1

It is certified that error appears in the above-identified patent and that said Letters Patent is hereby corrected as shown below:

In column 12, line 34, please change "read connector" to --lead connector--.

Signed and Sealed this

Ninth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,130,699 B2  
APPLICATION NO. : 10/436776  
DATED : October 31, 2006  
INVENTOR(S) : Huff et al.

Page 1 of 1

It is certified that error appears in the above-identified patent and that said Letters Patent is hereby corrected as shown below:

In column 12, line 34, please change "read connector" to --lead connector--.

This certificate supersedes Certificate of Correction issued October 9, 2007.

Signed and Sealed this

Thirtieth Day of October, 2007

JON W. DUDAS  
*Director of the United States Patent and Trademark Office*